(12) United States Patent
Kawai et al.

(10) Patent No.: US 8,188,326 B2
(45) Date of Patent: May 29, 2012

(54) PROCESS FOR PRODUCING ADAMANTANE

(75) Inventors: Takeshi Kawai, Niigata (JP);
Mitsuharu Kitamura, Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 12/736,653

(22) PCT Filed: May 7, 2009

(86) PCT No.: PCT/JP2009/058633
§ 371 (c)(1),
(2), (4) Date: Jan. 7, 2011

(87) PCT Pub. No.: WO2009/139317
PCT Pub. Date: Nov. 19, 2009

(65) Prior Publication Data
US 2011/0112346 A1      May 12, 2011

(30) Foreign Application Priority Data

May 14, 2008  (JP) .................................. 2008-127209

(51) Int. Cl.
*C07C 5/22*  (2006.01)
(52) U.S. Cl. .......................... 585/317; 585/352; 585/360
(58) Field of Classification Search .................. 585/317, 585/352, 360
See application file for complete search history.

(56) References Cited

U.S. PATENT DOCUMENTS
2,937,211 A    5/1960    Ludwig

FOREIGN PATENT DOCUMENTS

| JP | 36-005721 B1 | 5/1961 |
| JP | 55-038935 B2 | 10/1980 |
| JP | 2001-151705 A | 6/2001 |
| JP | 2008-019201 A | 1/2008 |

OTHER PUBLICATIONS

International Search Report mailed Jun. 9, 2009, in PCT/JP2009/058633, 2 pages.
Olah et al., "Superacid-Catalyzed Isomerization of endo- to exo-Trimethyleneorbornane (Tetrahydrodicyclopentadiene) and to Adamantane," J. Org. Chem., 1986, 51(26):5410-5413.

*Primary Examiner* — Thuan Dinh Dang
(74) *Attorney, Agent, or Firm* — Foley & Lardner LLP

(57) ABSTRACT

A method for producing adamantane by performing an isomerization reaction in two stages using endo-tetrahydrodicyclopentadiene and/or exo-tetrahydrodicyclopentadiene as a starting material, wherein in a first-stage isomerization reaction from endo-tetrahydrodicyclopentadiene (tricyclo[5.2.1.0$^{2,6}$]decane) to exo-tetrahydrodicyclopentadiene (tricyclo[5.2.1.0$^{2,6}$]decane), an HF catalyst alone or two catalysts of an HF catalyst and a BF$_3$ catalyst are used in the absence of a solvent; and in a second-stage isomerization reaction from exo-tetrahydrodicyclopentadiene (tricyclo[5.2.1.0$^{2,6}$]decane) to adamantane (tricyclo[3.3.1.1$^{3,7}$]decane), an HF catalyst and a BF$_3$ catalyst are used in the absence of a solvent.

5 Claims, 1 Drawing Sheet

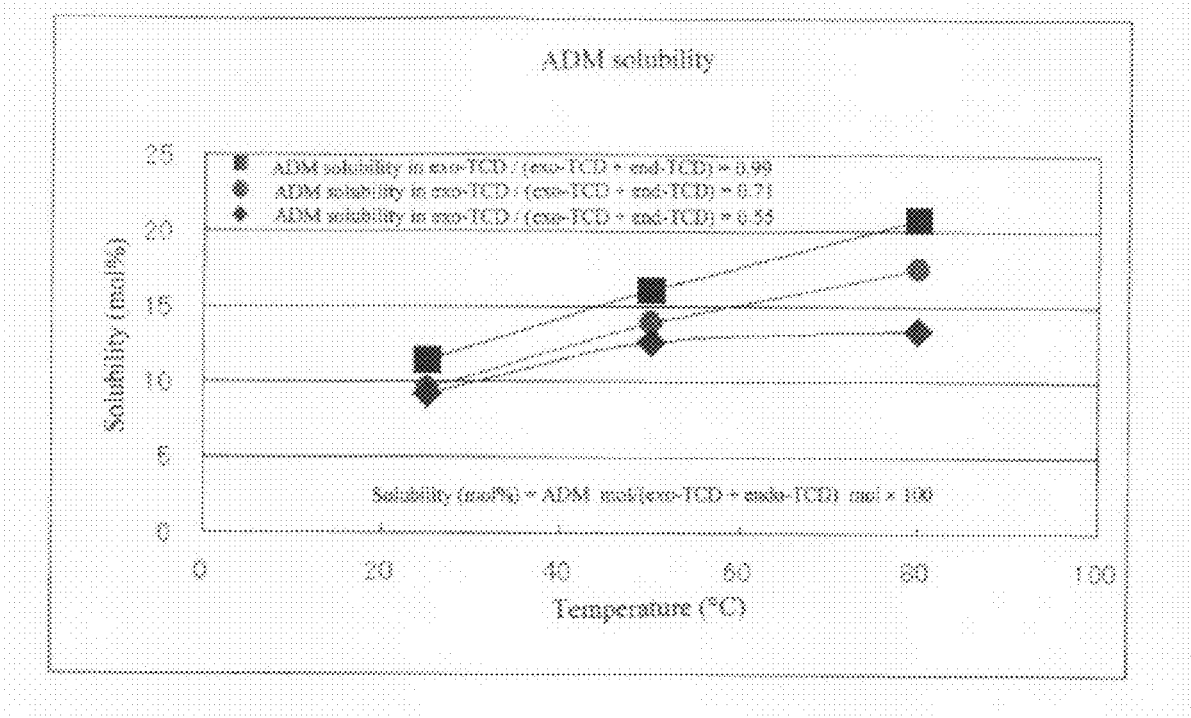

PROCESS FOR PRODUCING ADAMANTANE

CROSS-REFERENCE TO RELATED APPLICATIONS

This application is a National Stage application of PCT/JP2009/058633, filed May 7, 2009, which claims priority from Japanese application JP 2008-127209, filed May 14, 2008.

TECHNICAL FIELD

The present invention relates to a method for continuously producing adamantane (tricyclo[$3.3.1.1^{3,7}$]decane) in an industrially advantageous manner from endo-tetrahydrodicyclopentadiene (tricyclo[$5.2.1.0^{2,6}$]decane) and/or exo-tetrahydrodicyclopentadiene (tricyclo[$5.2.1.0^{2,6}$]decane) as a starting material using a specific catalyst in the absence of a solvent. Hereinafter, endo-tetrahydrodicyclopentadiene and/or exo-tetrahydrodicyclopentadiene will be occasionally referred to simply as "tetrahydrodicyclopentadiene".

BACKGROUND ART

Conventionally, many techniques for producing adamantane by isomerizing tetrahydrodicyclopentadiene under an acid catalyst are known (see, for example, Patent Documents 1 and 2). Especially, techniques for producing adamantane by isomerizing tetrahydrodicyclopentadiene using an HF catalyst and a $BF_3$ catalyst are well known (see, for example, Patent Documents 3 and 4, and Non-patent Document 1). However, the conventional techniques of using an HF catalyst and a $BF_3$ catalyst have the following defects. Where a large amount of adamantane is generated, adamantane is deposited as a solid. In order to obtain adamantane as a solid, the reactor needs to be opened. In the case where the reactor should be prevented from being opened, the deposited adamantane needs to be dissolved in a solvent to be formed into a solution, and so use of a solvent is unavoidable.

Patent Document 1: Japanese Patent Publication for Opposition No. S52-2909
Patent Document 2: Japanese Patent Publication for Opposition No. H03-031182
Patent Document 3: Japanese Patent Publication for Opposition No. S55-38935
Patent Document 4: Japanese Laid-Open Patent Publication No. 2001-151705
Non-patent Document 1: J. Org. Chem., Vol. 51, No. 26, 1986

DISCLOSURE OF THE INVENTION

An object of the present invention is to provide a method for producing adamantane continuously and industrially by isomerizing tetrahydrodicyclopentadiene without causing adamantane to be deposited as a solid even in the absence of a solvent other than tetrahydrodicyclopentadiene, which is a starting material.

As a result of accumulating active studies on an isomerization reaction using tetrahydrodicyclopentadiene, which is a starting material, the present inventors found a method for producing adamantane continuously and industrially with no need of a solvent other than tetrahydrodicyclopentadiene, which is a starting material, by controlling the yield of adamantane and putting a reaction product into a liquid phase, and thus achieved the present invention.

The present invention encompasses the following embodiments.

(1) A method for producing adamantane (tricyclo[$3.3.1.1^{3,7}$]decane) by performing an isomerization reaction in two stages using endo-tetrahydrodicyclopentadiene (tricyclo[$5.2.1.0^{2,6}$]decane) and/or exo-tetrahydrodicyclopentadiene (tricyclo[$5.2.1.0^{2,6}$]decane) as a starting material, comprising the steps of:

using an HF catalyst alone or two catalysts of an HF catalyst and a $BF_3$ catalyst in the absence of a solvent, in a first-stage isomerization reaction from endo-tetrahydrodicyclopentadiene (tricyclo[$5.2.1.0^{2,6}$]decane) to exo-tetrahydrodicyclopentadiene (tricyclo[$5.2.1.0^{2,6}$]decane); and using an HF catalyst and a $BF_3$ catalyst are used in the absence of a solvent, in a second-stage isomerization reaction from exo-tetrahydrodicyclopentadiene (tricyclo[$5.2.1.0^{2,6}$]decane) to adamantane (tricyclo[$3.3.1.1^{3,7}$]decane);

Scheme 1

[Chemical formula 1]

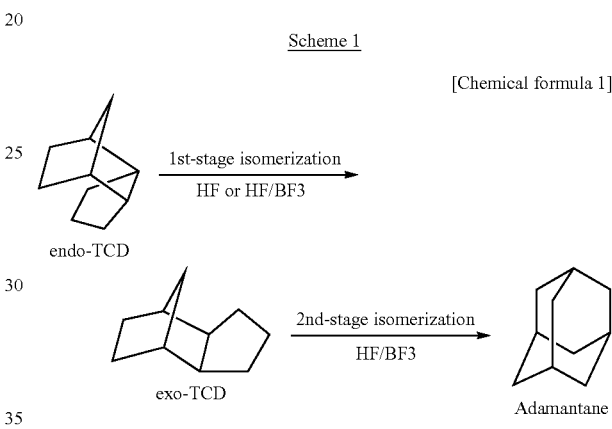

(2) The method for producing adamantane according to (1) above, wherein the first-stage isomerization reaction is performed while the ratio of exo-tetrahydrodicyclopentadiene (tricyclo[$5.2.1.0^{2,6}$]decane) in a reaction-produced solution obtained by the first-stage isomerization reaction is 0.9 parts by weight or greater with respect to 1 part by weight of a total amount of endo-tetrahydrodicyclopentadiene (tricyclo [$5.2.1.0^{2,6}$]decane) and/or exo-tetrahydrodicyclopentadiene (tricyclo[$5.2.1.0^{2,6}$]decane) as a starting material;

(3) The method for producing adamantane according to (1) or (2) above, wherein the HF catalyst or the two catalysts of the HF catalyst and the $BF_3$ catalyst are used for the first-stage isomerization reaction, and the $BF_3$ catalyst is further added for the second-stage isomerization reaction;

(4) The method for producing adamantane according to any one of (1) through (3) above, wherein 1.5 parts by weight or less of the HF catalyst and 0.02 to 0.5 parts by weight of the $BF_3$ catalyst are used with respect to 1 part by weight of the total amount of endo-tetrahydrodicyclopentadiene (tricyclo [$5.2.1.0^{2,6}$]decane) and/or exo-tetrahydrodicyclopentadiene (tricyclo[$5.2.1.0^{2,6}$]decane) as a starting material;

(5) The method for producing adamantane according to any one of (1) through (4) above, wherein un-isomerized exo-tetrahydrodicyclopentadiene (tricyclo[$5.2.1.0^{2,6}$]decane) is recovered and reused;

(6) The method for producing adamantane according to any one of (1) through (5) above, wherein the temperature is controlled such that a reaction temperature (T1, unit: ° C.) in the first-stage isomerization reaction and a reaction temperature (T2, unit: ° C.) in the second-stage isomerization reaction fulfill the following expressions (1) and (2).

$$0 \leq T1 \leq 50 \tag{1}$$

$$T1 \leq T2 \leq T1+30 \tag{2}$$

According to the method for producing adamantane of the present invention, for performing the isomerization reaction with the HF catalyst alone or the two catalysts of the HF catalyst and the $BF_3$ catalyst using tetrahydrodicyclopentadiene as a starting material, exo-tetrahydrodicyclopentadiene (hereinafter, occasionally referred to simply as "exo-TCD") is first synthesized, and then the yield of adamantane is controlled to be equal to or less than the total of the solubility of adamantane in exo-TCD and the solubility of adamantane in endo-tetrahydrodicyclopentadiene (hereinafter, occasionally referred to simply as "endo-TCD"). Owing to this, adamantane can be produced continuously and industrially without causing the generated adamantane to be deposited. The melting point of exo-TCD is −91° C., and exo-TCD is liquid at room temperature. Therefore, exo-TCD has a splendid characteristic as a solvent for dissolving the generated adamantane. By contrast, endo-TCD is solid at room temperature and so such a characteristic of endo-TCD is not splendid.

Where, for example, an aliphatic hydrocarbon other than exo-TCD and/or endo-TCD, which is a starting material, is used as a solvent, the solvent may be degenerated by an HF catalyst or a $BF_3$ catalyst, which are both a superstrong acid. However, the method according to the present invention does not use a solvent other than exo-TCD and/or endo-TCD, which is a starting material. Therefore, there is no need for the step of removing the solvent or a degenerated substance thereof, and so adamantane can be produced advantageously in terms of cost.

BRIEF DESCRIPTION OF THE DRAWINGS

FIG. 1 is a graph showing the measurement results of the solubility of adamantane (hereinafter, occasionally referred to simply as "ADM") in TCD (mol %=ADM mol/(exo-TCD+endo-TCD+ADM)mol×100).

BEST MODE FOR CARRYING OUT THE INVENTION

Hereinafter, the present invention will be described in detail.

The present invention is directed to a method for producing adamantane (tricyclo[3.3.1.1$^{3,7}$]decane) by performing an isomerization reaction in two stages using endo-tetrahydrodicyclopentadiene (tricyclo[5.2.1.0$^{2,6}$]decane) and/or exo-tetrahydrodicyclopentadiene (tricyclo[5.2.1.0$^{2,6}$]decane) as a starting material. As shown in the following scheme 1, in a first-stage isomerization reaction from endo-tetrahydrodicyclopentadiene (tricyclo[5.2.1.0$^{2,6}$]decane) to exo-tetrahydrodicyclopentadiene (tricyclo[5.2.1.0$^{2,6}$]decane), an HF catalyst alone or two catalysts of an HF catalyst and a $BF_3$ catalyst are used in the absence of a solvent. In a second-stage isomerization reaction from exo-tetrahydrodicyclopentadiene (tricyclo[5.2.1.0$^{2,6}$]decane) to adamantane (tricyclo[3.3.1.1$^{3,7}$] decane), an HF catalyst and a $BF_3$ catalyst are used in the absence of a solvent.

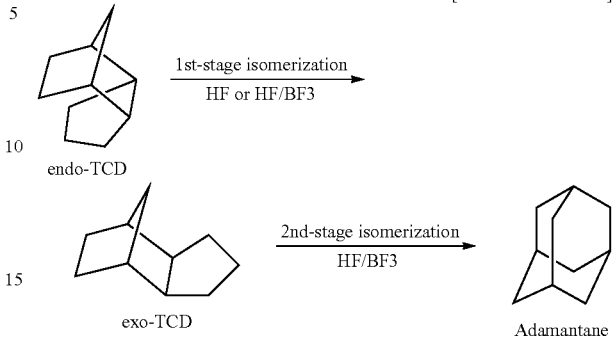

<Reaction scheme 1>
Scheme 1

[Chemical formula 2]

There are two types of TCD stereoisomers (exo-TCD, endo-TCD). In the present invention, exo-TCD alone, endo-TCD along, or a mixture thereof is usable as a starting material. TCD is generally obtained by water addition reaction of dicyclopentadiene (DCPD), which is a Diels-Adler reaction product of cyclopentadiene. By water addition reaction of dicyclopentadiene (DCPD), endo-TCD is obtained with priority (endo-rule, scheme 2).

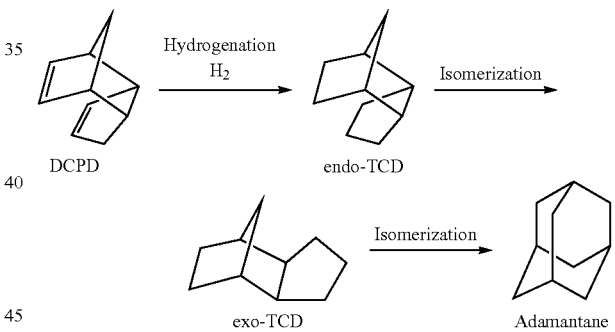

<Reaction scheme 2>
Scheme2

[Chemical formula 3]

However, the melting point of endo-TCD is as high as 78° C., and in order to treat 100% endo-TCD in a liquid phase, the temperature needs to be kept at the melting point or higher. By contrast, it is known that when an HF catalyst alone or two catalysts of an HF catalyst and a $BF_3$ catalyst are used, endo-TCD is isomerized into exo-TCD having a lower melting point (−91° C.). When this isomerization reaction is fully proceeded, TCD remaining the reaction solution is mostly exo-TCD. Herein, the "fully proceeded" does not mean that TCD obtains a high conversion (isomerization of endo-TCD→exo-TCD or change from TCD into another substance) or that adamantane is obtained at a high yield, but means that the yield of adamantane obtained under the isomerization reaction conditions according to the present invention after a sufficient residence time is higher than the yield of adamantane expectable with such conditions.

The present invention has enabled the two-stage isomerization reaction to occur in a liquid phase by isomerizing most of endo-TCD into exo-TCD and controlling the yield of adamantane, and thus enabled adamantane to be produced continuously and industrially. Isomerization of most of endo-TCD into exo-TCD specifically means that the ratio of exo-TCD in the reaction-produced solution obtained by the first-stage isomerization reaction is made 0.9 parts by weight or greater with respect to 1 part by weight of the total amount of endo-TCD and/or exo-TCD which is a starting material.

Depending on the reaction conditions, it is possible that adamantane is generated from exo-TCD before endo-TCD is isomerized into exo-TCD and as a result, a large amount of endo-TCD remains in the reaction-produced solution and thus the liquid phase is not obtained (endo-TCD has a melting point of 78° C., and is a solid at room temperature). The present invention has a technological feature in being capable of controlling such progress of the isomerization reaction. In the reaction-produced solution, exo-TCD having a low melting point effectively acts as a solvent. Therefore, when exo-TCD in the reaction-produced solution is recovered and reused, even where endo-TCD is newly provided as a starting material, the ratio of exo-TCD and endo-TCD needs to be controlled such that adamantane generated at the temperature of the reaction is dissolved. Namely, as the reaction temperature is lower and as the coexisting amount of endo-TCD is larger, the reaction-produced solution can be better kept in a liquid phase by increasing the amount of exo-TCD by the first-stage isomerization reaction. Furthermore, by recovering and reusing un-isomerized exo-TCD, the practical yield of adamantane can be increased (when the yield of adamantane is suppressed to be equal to or less than the solubility of adamantane in exo-TCD (e.g., 15 to 20 mol %), in consideration of the yield of adamantane obtained by the isomerization reaction of the recovered exo-TCD, the practical yield of adamantane selectivity of adamantane).

As shown by Schemes 1 and 2, the isomerization reaction occurs in the order of endo-TCD→exo-TCD→adamantane. The isomerization reaction of endo-TCD→adamantane does not occur. In a coexistence state in which exo-TCD having a high capability of dissolving adamantane is lost and endo-TCD having a low capability of dissolving adamantane remains, the risk of causing the trouble of adamantane being deposited as a solid is increased. The present invention has a technological feature that in that where the first-stage isomerization reaction of endo-TCD→exo-TCD is completed (the ratio of exo-TCD is 0.9 parts by weight or higher) and then the second-stage isomerization reaction of exo-TCD→adamantane is performed, the trouble of adamantane being deposited as a solid can be avoided.

When the reaction temperature is too high, the rate of isomerization reaction into adamantane is increased. In this case, adamantane is generated in an excessively large amount and is deposited as a solid. Therefore, the reaction temperature needs to be of a level at which the two-stage isomerization reaction is kept in a liquid phase and the yield of adamantane is suppressed low. In order to keep the two-stage isomerization reaction in a liquid phase, the yield of adamantane needs to be suppressed low. The first-stage isomerization is mainly the step of isomerizing most of endo-TCD into exo-TCD, and the second-stage isomerization is mainly the step of isomerizing exo-TCD into adamantane. Specifically, the reaction temperature for the first stage (T1) is preferably 0 to 50° C., and is more preferably 20 to 40° C. The reaction temperature for the second stage (T2) is preferably higher than the reaction temperature for the first stage (T1) by 0 to 30° C.

$$0 \leq T1 \leq 50 \quad (1)$$

$$T1 \leq T2 \leq T1+30 \quad (2)$$

When the reaction temperature for the second stage is equal to or higher by 0 to 30° C. than the reaction temperature for the first stage, the reaction rate is increased and so the yield of adamantane is improved. By contrast, when the reaction temperature for the second stage is too high, adamantane is deposited as a solid. In order to prevent adamantane from being deposited, the reaction time (residence time) needs to be controlled to be short, which is industrially difficult and is not practical. In addition, the selectivity of adamantane may be decreased. Therefore, an excessively high reaction temperature for the second stage is not preferable.

The reaction time (residence time) according to the present invention is preferably 1 to 15 hours, and more preferably 3 to 12 hours. When the reaction time is shorter than this range, the isomerization reaction from endo-TCD into exo-TCD is not progressed sufficiently, and so the yield of adamantane is not increased. When the reaction time is longer than this range, the yield of adamantane is increased, and so the risk of the trouble of adamantane being deposited as a solid is increased.

The HF catalyst is preferably used in the range of 1.5 parts by weight or less with respect to 1 part by weight of the total amount of endo-TCD and/or exo-TCD as a starting material, and more preferably used in the range of 0.3 to 1.2 parts by weight. When the HF catalyst is used at a ratio exceeding 1.5 parts by weight, adamantane is obtained at a high yield but the risk of adamantane being deposited as a solid is increased, and separation and recovery of the HF catalyst is costly. Therefore, a ratio of the HF catalyst which exceeds 1.5 parts by weight is not industrially practical.

The $BF_3$ catalyst is preferably used in the range of 0.02 to 0.5 parts by weight with respect to 1 part by weight of the total amount of endo-TCD and/or exo-TCD as a starting material, and more preferably used in the range of 0.05 to 0.3 parts by weight. When the $BF_3$ catalyst is used at a ratio exceeding 0.5 parts by weight, the yield of adamantane is increased but the risk of adamantane being deposited as a solid is increased, and a large amount of high boiling-point compound is generated as a by-product. In consideration of the cost required for the separation and purification step, a ratio of the $BF_3$ catalyst which exceeds 0.5 parts by weight is not industrially practical.

According to the present invention, it is preferable that an HF catalyst alone or two catalysts of an HF catalyst and a $BF_3$ catalyst are used for the first-stage isomerization reaction and a $BF_3$ catalyst is added thereto for the second-stage isomerization reaction. The HF catalyst used for the first-stage isomerization reaction also acts as an HF catalyst with no change in the second-stage isomerization reaction.

According to the present invention, it is preferable that there are facilities for re-supplying un-isomerized exo-TCD obtained in the separation and purification step back to the reactor.

After the isomerization reaction is terminated, the reaction product is kept still to be separated into two layers of an organic layer containing adamantane and an HF-$BF_3$ catalyst layer containing a high boiling-point compound generated as a by-product. Therefore, it is preferable that there are preferably facilities for performing liquid-liquid separation. Alternatively, the reaction product may be supplied to a distillation column in which a hydrocarbon such as heptane or the like is refluxed, thus to recover the HF and $BF_3$ catalysts from an apex portion of the column and an organic component containing adamantane from a bottom portion of the column, without performing the liquid-liquid separation.

According to the present invention, in order to allow the two-stage isomerization reaction to occur in a liquid phase, it is preferable that the yield (generation amount) of adamantane after the two-stage isomerization reaction is equal to or less than the total of the solubility thereof in exo-TCD and the solubility thereof in endo-TCD.

The present inventors confirmed through experiments that the ADM solubility in exo-TCD (S exo) is higher as the concentration of exo-TCD is higher (see FIG. 1), and found that such an ADM solubility fulfills the following expression (3) together with the reaction temperature (T, unit: ° C.).

$$S\,exo=0.169\times T+7.4 \quad (3)$$

The present inventors also found that the ADM solubility in endo-TCD (S endo) fulfills the following expression (4) together with the reaction temperature (T, unit: ° C.); and that expression (3) and expression (4) have additivity, namely, that total ADM solubility=ADM solubility (S exo)+ADM solubility (S endo).

$$S\,endo=0.071\times T+3.6 \quad (4)$$

Specifically, at 80° C., with respect to the purity of 80% of mixed TCD containing exo-TCD of 99% and endo-TCD of 1% (hereinafter, referred to simply as "exo-TCD (99)"), the total ADM solubility is 20 mol %. At 50° C., with respect to the purity of 84% of exo-TCD (99), the total ADM solubility is 16 mol %. At 25° C., with respect to the purity of 89% of exo-TCD (99), the total ADM solubility is 11 mol %. At 80° C., with respect to the purity of 81.5% of mixed TCD containing exo-TCD of 71% and endo-TCD of 29% (hereinafter, referred to simply as "exo-TCD (71)"), the total ADM solubility is 18.5 mol %. At 50° C., with respect to the purity of 86.1% of exo-TCD (71), the total ADM solubility is 13.9 mol %. At 25° C., with respect to the purity of 90.4% of exo-TCD (71), the total ADM solubility is 9.6 mol %. It is preferable to control the yield (generation amount) of adamantane to be equal to or less than such a level of ADM solubility.

The reaction-produced solution is obtained as a mixture of adamantane, exo-TCD, endo-TCD, a high boiling-point compound as a by-product, and a liquid containing an HF catalyst and a $BF_3$ catalyst. As described above, the reaction-produced solution, after being kept still, is separated into two layers of an organic layer containing adamantane and an HF-$BF_3$ catalyst layer containing a high boiling-point compound as a by-product. Thus, the organic layer can be obtained by liquid-liquid separation. The separated HF-$BF_3$ catalyst layer can be thermally recovered by being supplied to a distillation column in which a hydrocarbon (e.g., benzene, toluene, hexane, heptane, etc.) is refluxed. In this case, the $BF_3$ catalyst is obtained from an apex portion of the column, and the HF catalyst is obtained from a condenser in a bottom portion of the column.

Similarly, the organic component containing adamantane is obtained by supplying the entirety of the reaction-produced solution to a distillation column in which a hydrocarbon is refluxed. In this case, a solution containing the hydrocarbon is obtained from the bottom portion of the column.

The obtained organic component or organic layer containing adamantane is neutralized and rinsed with water to obtain a solution containing adamantane. Optionally, after the solvent is removed by distillation, adamantane may be purified by common means of cooling and crystallization or the like to separate and obtain adamantane.

EXAMPLES

Now, the present invention will be specifically described by way examples. The present invention is not limited to any of the following examples. The reaction products were each analyzed by a gas chromatography device (GC device) under the following conditions.

Device: GC-17A (produced by SHIMADZU Kabushiki Kaisha)

Column: HR-1 (produced by Shinwa Chemical Industries, Ltd.)

Analysis conditions: Injection Temp.: 310° C.; Detector Temp.: 310° C.

Column temperature: kept at 100° C. for 0 minute→raised to 320° C. at 5° C./min.→kept at 320° C. for 0 minute Detector: Hydrogen flame ionization detector (FID)

Method: The reaction-produced solution was extracted to a polypropylene receiver containing pure water (prepared by the company of the present inventors) and heptane (reagent: produced by Wako Pure Chemical Industries, Ltd.). In this step, as the amount of water, any amount sufficient with respect to the HF catalyst was usable. The standard for the amount of heptane was of three times the weight of TCD. Then, the substance in the polypropylene receiver was kept still to cause liquid-liquid separation. Thus, an organic layer containing adamantane was removed, washed once with a 2% aqueous solution of sodium hydroxide (sodium hydroxide: reagent produced by Wako Pure Chemical Industries, Ltd.; pure water: prepared by the company of the present inventors), and washed twice with warm water. To 1 g of the obtained organic layer, 0.1 g of dibenzyl (reagent: produced by Wako Pure Chemical Industries, Ltd.), which was the internal standard, was added, and the resultant substance was injected into the GC device. The TCD conversion, the yield of adamantane, and selectivity of adamantane were found based on the following expressions.

TCD conversion (mol %)=100−unreacted TCD (exo-TCD+endo-TCD)

Yield of adamantane (mol %)=Generation amount of adamantane

Selectivity of adamantane (mol %)=yield of adamantane/TCD conversion×100

Example 1

An isomerization reaction of TCD was performed using a continuous two-stage reactor including two hastelloy autoclaves connected to each other. Each autoclave has an internal volume of 0.5 L and includes an electromagnetic stirrer, a heater, a gas and liquid supply opening, and a reaction product discharge opening. Into the first-stage reactor, 300 g of HF catalyst (reagent: produced by Morita Chemical Industries, Co., Ltd.) was put, and into the second-stage reactor, 300 g of HF catalyst was put. The first-stage reactor was heated to 30° C. and the second-stage reactor was heated to 50° C. by the heater. Then, to the first-stage reactor, the following substances were supplied separately: TCD having an exo/endo isomer ratio of 0.285 and a purity of 99.2% (prepared by the company of the present inventors) at a ratio of 2.80 g/min., the HF catalyst at a ratio of 2.06 g/min., and a $BF_3$ catalyst (reagent: produced by Stella Chemifa Corporation) at a ratio of 0.14 g/min. The amount of the HF catalyst corresponded to 0.74 parts by weight, and the amount of the $BF_3$ catalyst corresponded to 0.05 parts by weight, with respect to 1 part by weight of TCD as the starting material. The average residence time was 1 hour.

Then, while the liquid surface in the first-stage reactor was kept constant, the liquid started to be transferred from the first-stage reactor to the second-stage reactor. At the same time, the flow rate was controlled to keep the liquid surface in the second-stage reactor constant. 4.5 hours after the starting material and the catalysts started to be supplied to the first-stage reactor (corresponding to 4.5 times the average residence time), sampling was performed. The composition of the reaction-produced solution in the first-stage reactor was exo-TCD: 86 mol %; adamantane: 9 mol %; and endo-TCD: 0.5 mol %. With respect to 1 part by weight of TCD as the starting material, the ratio of exo-TCD was 0.99 parts by weight (86/(86+0.5)=0.99) and the ratio of endo-TCD was 0.006 parts by weight (0.5/(86+0.5)=0.006). The composition of the reaction-produced solution in the second-stage reactor was exo-TCD: 75 mol %; adamantane: 15.5 mol %; and endo-TCD: 0.5 mol %. With respect to 1 part by weight of TCD as the starting material, the ratio of exo-TCD was 0.99 parts by weight (75/(75+0.5)=0.99) and the ratio of endo-TCD was 0.007 parts by weight (0.5/(75+0.5)=0.007). Based on the composition of the reaction-produced solution after the two-stage continuous isomerization reaction, the TCD conversion was 100−(75+0.5)=24.5 mol %, the yield of adamantane was 15.5 mol %, and the selectivity of adamantane was 15.5/24.5×100=63.2 mol %.

Example 2

The same procedure as in Example 1 was performed except that TCD which was endo-TCD having a purity of 99.5% was used as a starting material. The composition of the reaction-produced solution in the first-stage reactor was exo-TCD: 87 mol %; adamantane: 9 mol %; and endo-TCD: 0.8 mol %. With respect to 1 part by weight of TCD as the starting material, the ratio of exo-TCD was 0.99 parts by weight (87/(87+0.8)=0.99) and the ratio of endo-TCD was 0.009 parts by weight (0.8/(87+0.8)=0.009). The composition of the reaction-produced solution in the second-stage reactor was exo-TCD: 75 mol %; adamantane: 15.2 mol %; and endo-TCD: 0.5 mol %. With respect to 1 part by weight of TCD as the starting material, the ratio of exo-TCD was 0.99 parts by weight (75/(75+0.5)=0.99) and the ratio of endo-TCD was 0.007 parts by weight (0.5/(75+0.5)=0.007). Based on the composition of the reaction-produced solution after the two-stage continuous isomerization reaction, the TCD conversion was 100−(75+0.5)=24.5 mol %, the yield of adamantane was 15.2 mol %, and the selectivity of adamantane was 15.2/24.5×100=62.0 mol %.

Example 3

The same procedure as in Example 1 was performed except that TCD which was exo-TCD having a purity of 99.4% was used as a starting material. The composition of the reaction-produced solution in the first-stage reactor was exo-TCD: 86 mol %; and adamantane: 10 mol %. With respect to 1 part by weight of TCD as the starting material, the ratio of exo-TCD was 1.00 parts by weight (86/(86+0)=1.00). The composition of the reaction-produced solution in the second-stage reactor was exo-TCD: 75 mol %; and adamantane: 15.6 mol %. Based on the composition of the reaction-produced solution after the two-stage continuous isomerization reaction, the TCD conversion was 100−75=25 mol %, the yield of adamantane was 15.2 mol %, and the selectivity of adamantane was 15.2/25×100=60.8 mol %.

Example 4

The same procedure as in Example 1 was performed except that TCD which was recovered exo-TCD having a purity of 98.0% was used as a starting material. The composition of the reaction-produced solution in the first-stage reactor was exo-TCD: 84 mol %; and adamantane: 10 mol %. With respect to 1 part by weight of TCD as the starting material, the ratio of exo-TCD was 1.00 parts by weight (84/(84+0)=1.00). The composition of the reaction-produced solution in the second-stage reactor was exo-TCD: 72 mol %; and adamantane: 15.4 mol %. Based on the composition of the reaction-produced solution after the two-stage continuous isomerization reaction, the TCD conversion was 100−72=28 mol %, the yield of adamantane was 15.2 mol %, and the selectivity of adamantane was 15.2/28×100=54.3 mol %.

Example 5

An isomerization reaction was performed using similar facilities to those in Example 1. Into the first-stage reactor, 300 g of HF catalyst (reagent: produced by Morita Chemical Industries, Co., Ltd.) was put, and into the second-stage reactor, 300 g of HF catalyst was put. The first-stage reactor was heated to 50° C. and the second-stage reactor was heated to 50° C. by the heater. Then, to the first-stage reactor, the following substances were supplied: TCD having an exo/endo isomer ratio of 0.285 and a purity of 99.2% (prepared by the company of the present inventors) at a ratio of 1.11 g/min., and the HF catalyst at a ratio of 0.50 g/min. The amount of the HF catalyst corresponded to 4.4 parts by weight with respect to 1 part by weight of TCD as the starting material. The average residence time was 8.2 hours.

Then, while the liquid surface in the first-stage reactor was kept constant, the liquid started to be transferred from the first-stage reactor to the second-stage reactor. A $BF_3$ catalyst (reagent: produced by Stella Chemifa Corporation) was supplied at a ratio of 0.01 g/min. (corresponding to 0.01 parts by weight of $BF_3$ with respect to 1 part by weight of TCD as the starting material; the average residence time: 8.2 hours). At the same time, the flow rate was controlled to keep the liquid surface in the second-stage reactor constant. 12 hours after the starting material and the catalyst started to be supplied to the first-stage reactor (corresponding to 1.5 times the average residence time), sampling was performed. The composition of the reaction-produced solution in the first-stage reactor was exo-TCD: 86 mol %; adamantane: 0.3 mol %; and endo-TCD: 8.9 mol %. With respect to 1 part by weight of TCD as the starting material, the ratio of exo-TCD was 0.91 parts by weight (86/(86+8.9)=0.91) and the ratio of endo-TCD was 0.094 parts by weight (8.9/(86+8.9)=0.094). The composition of the reaction-produced solution in the second-stage reactor was exo-TCD: 76 mol %; adamantane: 14.9 mol %; and endo-TCD: 0.5 mol %. With respect to 1 part by weight of TCD as the starting material, the ratio of exo-TCD was 0.99 parts by weight (76/(76+0.5)=0.99) and the ratio of endo-TCD was 0.007 parts by weight (0.5/(76+0.5)=0.007). Based on the composition of the reaction-produced solution after the two-stage continuous isomerization reaction, the TCD conversion was 100−(76+0.5)=23.5 mol %, the yield of adamantane was 14.9 mol %, and the selectivity of adamantane was 14.9/23.5×100=63.4 mol %.

Comparative Example 1

The procedure was performed under the same conditions as in Example 1 except that the isomerization reaction was performed using only the second-stage reactor at 50° C. without using the first-stage reactor. As a result, 1 hour after the starting material and the catalysts started to be supplied to the reactor, the exit opening of the second-stage reactor was clogged. The exit opening of the reactor was opened and the reaction-produced solution was analyzed. The composition of the reaction-produced solution was exo-TCD: 45.0 mol %;

yield of adamantane: 15.0 mol %; and endo-TCD: 30.5 mol %. The total ADM solubility of adamantane with respect to TCD calculated based on expressions (3) and (4) is 12.3 mol %. The above results show that the yield (generation amount) of adamantane exceeded this solubility and so was deposited as a solid and clogged the opening.

The invention claimed is:

1. A method for producing adamantane (tricyclo[3.3.1.1$^{3,7}$]decane) by performing an isomerization reaction in two stages using endo-tetrahydrodicyclopentadiene (tricyclo[5.2.1.0$^{2,6}$]decane) or a mixture of endo-tetrahydrodicyclopentadiene (tricyclo[5.2.1.0$^{2,6}$]decane) and exo-tetrahydrodicyclopentadiene (tricyclo[5.2.1.0$^{2,6}$]decane) as a starting material; comprising the steps of:

producing exo-tetrahydrodicyclopentadiene (tricyclo[5.2.1.0$^{2,6}$]decane) from endo-tetrahydrodicyclopentadiene (tricyclo[5.2.1.0$^{2,6}$]decane) using an HF catalyst alone or two catalysts of an HF catalyst and a BF$_3$ catalyst in the absence of a solvent in a first-stage reactor for a first-stage isomerization reaction; and producing adamantine (tricyclo[3.3.1.1$^{3,7}$]decane) from the exo-tetrahydrodicyclopentadiene (tricyclo[5.2.1.0$^{2,6}$]decane) using an HF catalyst and a BF$_3$ catalyst in the absence of a solvent in a second-stage reactor for a second-stage isomerization reaction wherein the temperature is controlled such that a reaction temperature (T1, unit: ° C.) in the first-stage isomerization reaction and a reaction temperature (T2, unit: ° C.) in the second-stage isomerization reaction fulfill the following expressions (1) and (2)

$$0 \leq T1 \leq 50 \quad (1)$$

$$T1 \leq T2 \leq T1+30 \quad (2).$$

2. The method for producing adamantane according to claim 1, wherein the first-stage isomerization reaction is performed while the ratio of exo-tetrahydrodicyclopentadiene (tricyclo[5.2.1.0$^{2,6}$]decane) in a reaction-produced solution obtained by the first-stage isomerization reaction is 0.9 parts by weight or greater with respect to 1 part by weight of a total amount of endo-tetrahydrodicyclopentadiene (tricyclo[5.2.1.0$^{2,6}$]decane) and exo-tetrahydrodicyclopentadiene (tricyclo[5.2.1.0$^{2,6}$]decane) as a starting material.

3. The method for producing adamantane according to claim 1, wherein the HF catalyst or the two catalysts of the HF catalyst and the BF$_3$ catalyst are used for the first-stage isomerization reaction, and the BF$_3$ catalyst is further added for the second-stage isomerization reaction.

4. The method for producing adamantane according to claim 1, wherein 1.5 parts by weight or less of the HF catalyst and 0.02 to 0.5 parts by weight of the BF$_3$ catalyst are used with respect to 1 part by weight of the total amount of endo-tetrahydrodicyclopentadiene (tricyclo[5.2.1.0$^{2,6}$]decane) and exo-tetrahydrodicyclopentadiene (tricyclo[5.2.1.0$^{2,6}$]decane) as a starting material.

5. The method for producing adamantane according to claim 1, wherein un-isomerized exo-tetrahydrodicyclopentadiene (tricyclo[5.2.1.0$^{2,6}$]decane) is recovered and reused.

* * * * *